United States Patent [19]

Chang et al.

[11] Patent Number: 5,235,179
[45] Date of Patent: Aug. 10, 1993

[54] EVANESCENT WAVE LIQUID LEVEL SENSOR WITH DENSITY COMPENSATION

[75] Inventors: David B. Chang, Tustin; Victor Vali, Laguna Hills; Keith V. Pearson, Long Beach; Albert F. Lawrence, San Diego, all of Calif.

[73] Assignee: Hughes Aircraft Company, Los Angeles, Calif.

[21] Appl. No.: 764,754

[22] Filed: Sep. 24, 1991

[51] Int. Cl.$^5$ .................. H01J 5/16; G01N 15/06
[52] U.S. Cl. .................. 250/227.21; 250/575; 250/577; 250/905; 250/900
[58] Field of Search .......... 250/577, 575, 574, 900, 250/902, 904, 905, 906, 907, 227.21, 227.25, 231.19, 231.1; 73/293; 340/619; 385/12

[56] References Cited

U.S. PATENT DOCUMENTS

| | | | |
|---|---|---|---|
| 3,995,169 | 11/1976 | Oddon | 250/577 |
| 4,240,747 | 12/1980 | Harmer | 250/577 |
| 4,287,427 | 9/1981 | Scifres | 250/577 |
| 4,598,742 | 7/1986 | Taylor | 250/577 |
| 4,893,894 | 1/1990 | Caimi | 385/12 |
| 5,026,984 | 6/1991 | Gerdt | 250/227.21 |
| 5,058,420 | 10/1991 | Vali et al. | 250/577 |

*Primary Examiner*—David C. Nelms
*Assistant Examiner*—Michael Messinger
*Attorney, Agent, or Firm*—Elizabeth E. Leitereg; Terje Gudmestad; W. K. Denson-Low

[57] ABSTRACT

An evanescent wave liquid level sensor for measuring the density-compensated level of a liquid in a container. The sensor employs an eccentric core optical fiber fully immersed in the liquid to be measured. Light is injected into one end of the fiber. Some of the light will be lost due to evanescent wave losses. Changes in the ratio of the intensity of the input light and the reflected light are due solely to changes in the density of the liquid. Changes in the liquid density can then be used to compensate a liquid level measurement. Since the liquid temperature is related to its density, the sensor can also be used to measure changes in the liquid temperature.

20 Claims, 2 Drawing Sheets

EVANESCENT WAVE LIQUID LEVEL SENSOR WITH DENSITY COMPENSATION

BACKGROUND OF THE INVENTION

The present invention relates to apparatus for measuring the level and density of liquids.

The invention is related to application Ser. No. 07/484,295, now U.S. Pat. No. 5,077,482, by Victor Vali et al., entitled "Fiber Optic Fuel and Liquid Gauge" filed Feb. 23, 1990 and assigned to a common assignee with the present application. This pending application is incorporated herein in its entirety by this reference. The fiber optic liquid level sensor described in this pending application can be used as a leak detector for underground storage tanks, but only if the liquid temperature or density is simultaneously measured. This measurement is required to compensate for any change in the liquid volume not associated specifically with liquid entering or leaving the tank.

There are many previous techniques of measuring the temperature of a liquid, including thermistors, thermometers, thermocouplers, Mach Zehnder fiber optic thermometers, etc. The problem with these previous approaches is that the necessary accuracy for compensation of the density variation described above is very great. This requires heroic measures in fabrication and calibration.

Methods of measuring pressure accurately include Mach Zehnder fiber optic pressure gauges and piezoelectric devices. Again, the former is expensive to make and the latter measures only changes in time.

It is therefore an object of the present invention to provide a simple apparatus for measuring the density of liquids to compensate for the effects of density and temperature changes on a liquid level measurement.

SUMMARY OF THE INVENTION

A liquid level sensor system for measuring the level of liquid within a container is described, and which includes a means for compensating for liquid density changes. The system includes a level sensor optical fiber disposed within the container and extending through the range of liquid surface positions to be measured by the system. The level sensor fiber has an inner fiber core and an outer fiber cladding. The cladding thickness is appropriate to provide significant evanescent wave loss when the cladding is immersed in the liquid.

A density sensor optical fiber is positioned to be completely immersed in the liquid. The density sensor fiber has an inner fiber core and an outer fiber cladding. The cladding thickness is appropriate to provide significant evanescent wave loss when the cladding is immersed in the liquid.

The system further comprises means for injecting input light into the level sensor fiber and for injecting input light into the density sensor fiber. A means is provided for determining the loss of light traversing the level sensor fiber at least once to provide an indication of the nominal liquid level in the container.

The system further comprises a means for determining the loss of light traversing the density sensor fiber, and a processing means responsive to the respective loss determining means for compensating the nominal liquid level by any changes in the liquid density to provide a compensated liquid level value.

In one form, the means for determining the loss of light passing through the respective sensor fibers comprises means for determining a ratio value of input light intensity to the intensity of light which has passed through the respective sensor fibers at least once.

A method for measuring the level of liquid within a container in accordance with the invention is also described, and comprises the following steps:

positioning a level sensor optical fiber within the container so that it extends through the range of liquid surface positions to be measured, wherein the fiber has an inner fiber core and an outer fiber cladding, the thickness of fiber cladding being selected to provide significant evanescent wave loss when the cladding is immersed in the liquid;

completely immersing a density sensor optical fiber in the liquid, the density sensor fiber having an inner fiber core and an outer fiber cladding, the thickness of fiber cladding being selected to provide significant evanescent wave loss when the cladding is immersed in the liquid;

injecting input light into the respective sensor fibers;

determining the loss of light which has passed through the level sensor fiber at least once;

determining the loss of light which has passed through the density sensor fiber at least once; and processing the respective light losses to provide a signal indicative of the liquid level in the container and which is compensated for changes in the density of the liquid level.

BRIEF DESCRIPTION OF THE DRAWING

These and other features and advantages of the present invention will become more apparent from the following detailed description of an exemplary embodiment thereof, as illustrated in the accompanying drawings, in which.

DETAILED DESCRIPTION OF THE PREFERRED EMBODIMENT

The above referenced pending application describes a method for measuring the length of an optical fiber immersed in a liquid. When the cladding thickness of an optical fiber is only a few wavelengths of light, as in an eccentric core fiber, the evanescent wave extends outside the fiber cladding. If such a fiber is covered by or immersed in a liquid with index of refraction larger than that of the fiber cladding, some of the light leaks out of the fiber core. This effect can be used to determine the height of the liquid level in a container, as described in the referenced pending application. Eccentric core fibers can be made so that the cladding thickness is less than 5 micrometers, thus providing significant evanescent wave losses.

The principle of operation of the fiber optic evanescent wave liquid density sensor in accordance with this invention is based on the observation that the absorption coefficient $\alpha$ of light transmitted through a liquid is proportional to the liquid density. Therefore, the intensity I of the radiation transmitted through an eccentric core fiber is described by $$I = I_0 e^{-\alpha x} \quad (1)$$

where $I_0$ is the initial intensity and x is the length of the fiber in the liquid. If x is kept constant (i.e., keeping all of the fiber in the liquid) the variation of $\alpha$ is measured as a function of the density.

Since the density of a liquid is a function of temperature, the apparatus can also function as a temperature gauge. The density, pressure and temperature of a liquid are related in the following manner.

$$(\delta\rho/\rho) = (1/\rho)(\partial\rho/\partial T)_P \delta T + (1/\rho)(\partial\rho/\partial P)_T \delta P \quad (2)$$

where T is the temperature of the liquid, P is the pressure and $\rho$ is the liquid density.

For a typical liquid $(\partial\rho/\partial T)_P$ is $10^{-4}\ °C^{-1}$ and $(\partial\rho/\partial P)_T$ is much smaller.

Figure 1:
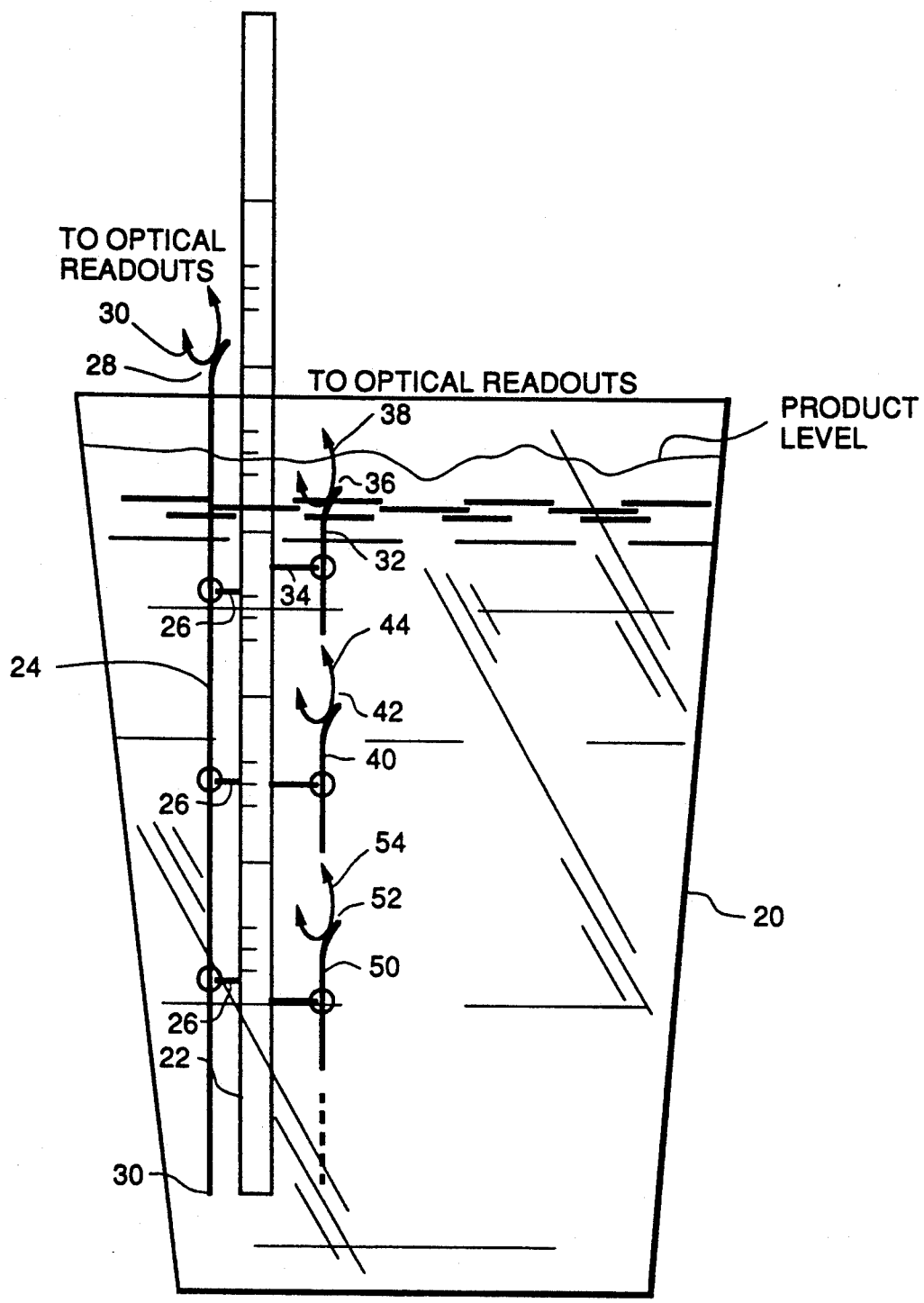
FIG. 1 illustrates in simplified form a sensor apparatus in accordance with the invention and including a plurality of density sensors for measuring density changes at a plurality of liquid depths.

FIG. 1 illustrates one exemplary optical fiber sensor arrangement of a liquid level and density measuring system in accordance with the invention. Within the liquid container 20, a support pole 22 supports the optical fiber sensor elements. Optical fiber 24 is supported by bracket 26 extending from the support pole 22, and is partially immersed in the liquid. The fiber 24 is an eccentric core fiber. An optical coupler 28 couples input light from a light source (not shown in FIG. 1) into the fiber 24 and provides a means for coupling light reflected from the immersed end 30 to a detector and readout circuit. Thus, the sensor elements 24 and 28 comprise a liquid level measuring system of the type described in the above referenced pending application.

The system further comprises a density sensor element for determining the density of the liquid, and thereby providing a means for compensating for temperature changes in the liquid. Three different density sensors, each at different depths in the liquid, are illustrated in the exemplary embodiment of FIG. 1. Eccentric core fiber 32 is fully immersed in the liquid, and is attached to the support pole 22 by a bracket 34. An optical coupler 36 provides a means of coupling light between the sensor fiber 32 and an input/output optical fiber 38 which extends from the light source (not shown in FIG. 1) and the readout elements. The density sensor operates in exactly the same manner as the liquid level sensor, with the readout elements indicating the evanescent light loss, except that any change in light loss is due to a change in the liquid density and not due to a change in liquid level, since the fiber 32 remains immersed in the liquid at all times. The fiber 38 is of a type, e.g., a concentric core fiber, which does not permit significant evanescent wave loss to the surrounding liquid, and therefore it does not influence the density sensor reading accuracy.

Two additional density sensors are included in the arrangement of FIG. 1. Eccentric core sensor fiber 40 is fastened to the support pole 22 at a lower depth than the sensor fiber 32. An optical coupler 42 couples light between the sensor fiber 32 and the fiber 44 which extends from the light source and readout elements for this sensor. Another eccentric core sensor fiber 50 is attached to the support pole 22 at a lower depth than the sensor fiber 40. An optical coupler 52 couples light between this sensor fiber 50 and the input/output optical fiber 54 which extends from the light source and readout elements for this source. Additional density sensor elements could be employed at additional depths if required for a particular application. For deep liquids, the density would be expected to vary with depth, and this type of information might be useful for sensors which sample a variety of depths.

This scheme can be used to compensate for varying temperature changes in a tank of circular or irregular cross-section. In this embodiment the sensor which is partially immersed in the liquid serves as a level detector, and the ones below which are fully immersed serve as density detectors. The temperature changes cause density changes in the liquid. It is important to know how much of the attenuation measured over the length of the liquid level sensor fiber is due to a change in the liquid level intentional leakage or due to liquid removal, and how much is due to density change. Since the evanescent wave loss per unit length of the sensor fiber(s) immersed in the liquid is proportional to the density, the density change can be measured directly, and the part of the attenuation measured by the level sensor which is associated with density changes can be determined directly.

The liquid level sensor shown in FIG. 1 comprises a fiber 24 which extends substantially along the entire depth of the container 20. As the liquid level decreases, eventually the density sensing fiber 32 will no longer be completely immersed in the liquid. The liquid level sensor comprising fiber 24 can indicate when the level of the fluid drops to a point at which the density sensing fiber 32, and eventually the other density fibers 40, 50, etc. are no longer immersed. When a level has been reached at which a particular density sensing fiber is no longer completely immersed, as indicated by the coarse level indicated by the level sensing fiber, that density sensing fiber readout will be disregarded by the controller receiving the readouts from the respective level and density sensors. In the alternative, the liquid level sensor extends only over a small range, wherein it is expected that all density sensors are completely immersed throughout the level range to be covered by the level sensor.

Figure 2:
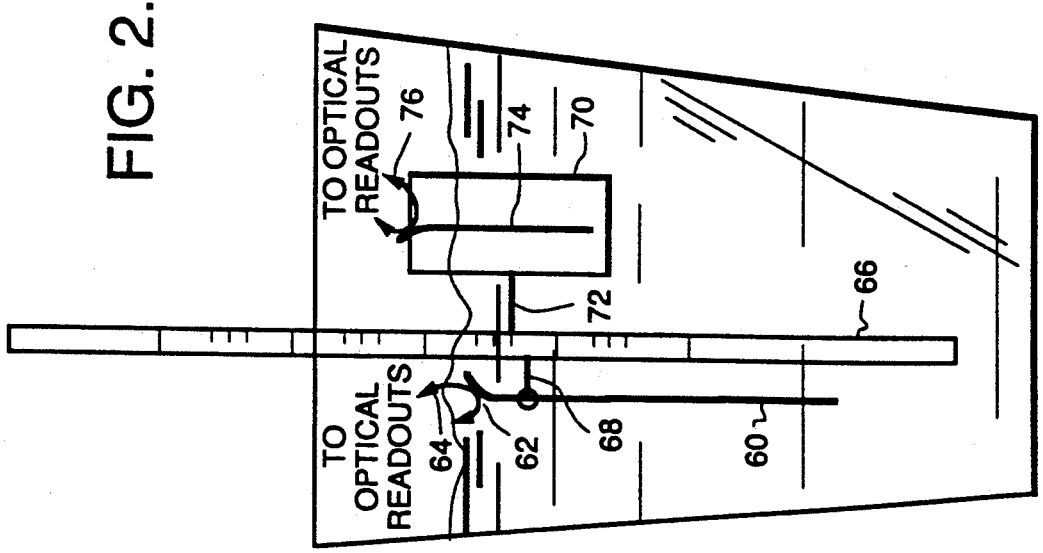
FIG. 2 illustrates in simplified form a sensor apparatus for measuring the level of liquid in a container and employing liquid density compensation.

FIG. 2 illustrates a second embodiment of a measuring system embodying the invention. In this system, the height of a first sensor element is adjusted relative to the rod 66 so that the first sensor element is completely immersed in the liquid when the rod has been inserted into the fluid container so that its end rests on the bottom of the container. This sensor serves as a density detector. The height of a second sensor is adjusted so that the second sensor element is partially immersed. With appropriate conversion, the second sensor serves as a level detector.

This embodiment is particularly suited to an application such as a leak detecting system for a container such as an underground fuel storage container. Such a system may employ a rod 66 which is inserted into the container for the purpose of making a level or leak detecting measurement. The height of the first sensor is adjusted so that the first sensor element is completely immersed in the liquid. The height of the second sensor is adjusted so that it is only partially immersed. At this point, the system is ready to monitor any leaks in the liquid container. By monitoring the level of liquid sensed by the level sensing fiber as compensated by the density sensor, the liquid level can be monitored for any density-compensated changes, indicating that liquid is leaking from the container.

The first sensor comprises the sensing fiber 60, which is an eccentric core fiber, an optical coupler 62 and input/output fiber 64 which connects to the light source and readout elements. The fiber 60 is fastened to a support pole 66 by, e.g., by one or more support elements 68. The vertical position of the fiber 60 may be adjusted upwardly or downwardly, by raising or lowering the support pole 66, in order to properly position the fiber 60 so that it is completely immersed in the liquid. Thus, the first sensor serves as a density detector; with appropriate conversion using the relationship of eq. 2, the sensor can also serve to measure temperature changes.

The second sensor comprises eccentric core optical fiber 70 which is fastened by fastener 72 to the support pole 66 at a position so that the fiber 70 is only partially immersed in the liquid. An optical coupler 74 couples light between the input/output fiber 76 which runs to the light source and readout elements. The vertical position of the fiber 70 can be adjusted upwardly or downwardly so that it remains only partially immersed in the liquid.

As in the embodiment of FIG. the input/output optical fibers 64 and 76 are fibers such as concentric core fibers which do not have significant evanescent wave losses.

In the system of FIG. 2, the density changes in the liquid as detected by the density sensor can be employed to compensate the liquid level sensor for density changes. The liquid level change $\delta l$ due to density change is given by eq. 3.

$$\delta l \simeq -(\rho(l)A(l))/\int_0^l \delta\rho(h)A(h)dh \quad (3)$$

where A(h) is the cross sectional area of the tank at a height h from the bottom, l is the height of the liquid level above the tank bottom, A(l) is the cross-sectional area of the tank at a height l, and p is the pressure.

Figure 3:
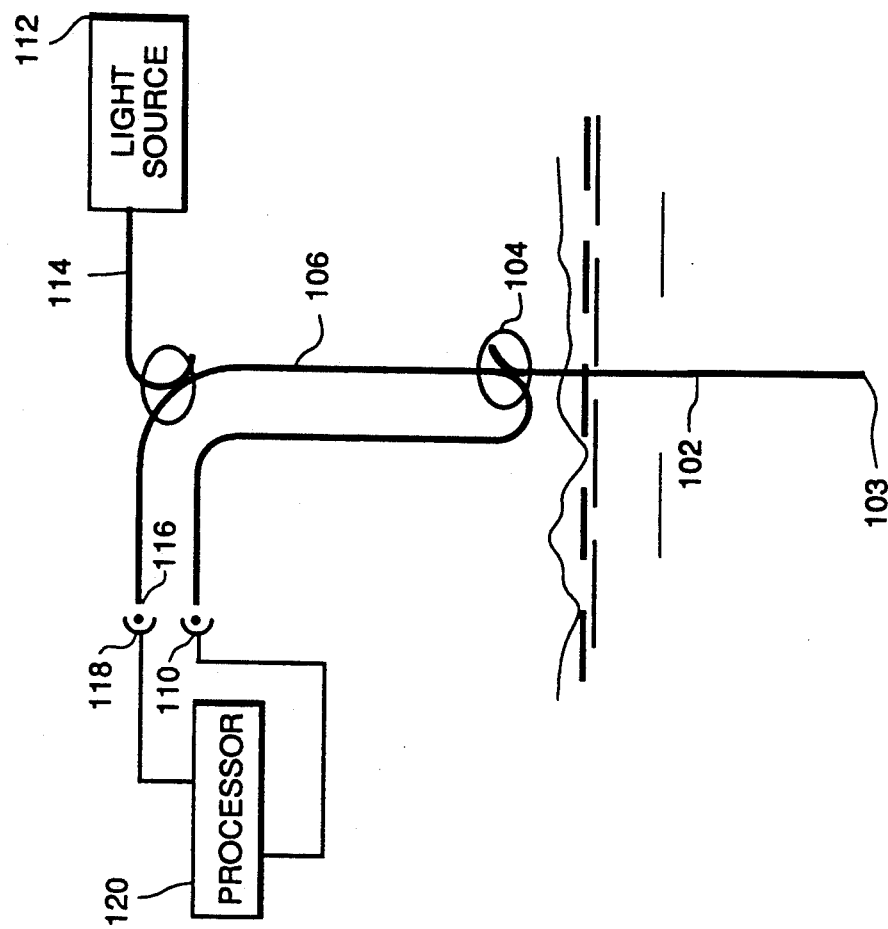
FIG. 3 shows an exemplary arrangement of the light source and readout elements usable in the systems of FIGS. 1 and 2.

FIG. 3 illustrates a simplified schematic block diagram of a the light source and readout configuration usable with the sensors of FIG. 1 and 2. The sensor fiber 102 is the eccentric core fiber which is characterized by significant evanescent wave losses when immersed in the liquid. An optical coupler 104 couples light between the sensor fiber 102 and the input/output fiber 104. One end 108 of the input/output fiber 106 is terminated in a photodetector 110 for detecting the intensity of the input light intensity. A second optical coupler couples light into the fiber 106 from the light source 112 via optical fiber 114. Both the fibers 106 and 114 are concentric core fibers which do not exhibit significant evanescent wave losses when immersed in liquid. A second end 116 of the fiber 106 is connected to a second photodetector 118 for detecting the intensity of the light backscattered from the sensor fiber end 103. A processor 120 is responsive to the photodetector outputs to process the relative intensity ratio, to determine the liquid density, level or temperature, depending on the particular function of the sensor fiber 102. A single light source may be used to provide the input light to the various sensors with beamsplitters used to split the light to the various sensor fibers.

The invention also takes the form of a method for measuring the level of liquid within a container. The method includes the following steps:

positioning a level sensor optical fiber within the container so that it extends through the range of liquid surface positions to be measured, wherein the fiber has an inner fiber core and outer fiber cladding, the thickness of fiber cladding being selected to provide significant evanescent wave loss when the cladding is immersed in the liquid;

completely immersing a density sensor optical fiber in the liquid, the density sensor fiber having an inner fiber core and outer fiber cladding, the thickness of the fiber cladding being selected to provide significant evanescent wave loss when the cladding is immersed in the liquid;

injecting input light into the respective sensor fibers;

determining the loss of light which has passed through the level sensor fiber at least once;

determining the loss of light which has passed through the density sensor fiber at least once; and processing the respective light losses to provide a signal indicative of the liquid level in the container and which is compensated for changes in the density of the liquid level.

It is understood that the above-described embodiments are merely illustrative of the possible specific embodiments which may represent principles of the present invention. Other arrangements may readily be devised in accordance with these principles by those skilled in the art without departing from the scope and spirit of the invention.

What is claimed is:

1. A liquid level sensor for measuring the level of liquid within a container and with compensation for liquid density changes, comprising:

a level sensor optical fiber disposed within said container and extending through the range of liquid surface positions to be measured by the system, wherein said level sensor fiber is characterized by an inner fiber core and an outer fiber cladding, the cladding thickness appropriate to provide significant evanescent wave loss when the cladding is immersed in the liquid;

a first density sensor optical fiber positioned to be completely immersed in said liquid, said density sensor fiber characterized by an inner fiber core and an outer fiber cladding, the cladding thickness appropriate to provide significant evanescent wave loss when the cladding is immersed in the liquid;

means for injecting light into said level sensor fiber and for injecting light into said density sensor fiber;

means for determining the loss of light traversing said level sensor fiber at least once to provide an indication of the nominal liquid level;

means for determining the loss of light traversing said density sensor fiber; and processing means responsive to said respective loss determining means for compensating said nominal liquid level by any changes in the liquid density to provide a compensated liquid level value.

2. The system of claim 1 wherein said means for determining the loss of light traversing said level sensor fiber comprises means for determining a first ratio value of input light intensity to the intensity of light which has passed through said level sensor fiber at least once.

3. The system of claim 2 wherein said means for determining the loss of light traversing said density sensor fiber comprises means for determining a second ratio value of input light intensity to the intensity of light which has passed through said density sensor fiber at least once.

4. The system of claim 3 wherein said processing means is responsive to said first and second ratio values to determine said compensated liquid level value.

5. The system of claim 1 wherein said level sensor and density sensor optical fibers comprise eccentric core fibers.

6. The system of claim 1 further comprising a second density optical fiber completely immersed in the liquid and positioned at a different depth than said first density sensor fiber, said second fiber characterized by an inner fiber core and an outer cladding, the cladding thickness appropriate to provide significant evanescent wave loss when the cladding is immersed in the liquid, means for injecting input light into said second fiber, means for determining the loss of light passing through said second fiber at least once; and wherein said processing means further comprises means for compensating said nominal liquid level by changes in the density of the liquid at said depth of said second fiber.

7. A liquid level sensor for measuring the level of liquid within a container and with compensation for liquid density, comprising:
   a level sensor optical fiber disposed within said container and extending through the range of liquid surface positions to be measured by the system, wherein said level sensor fiber is characterized by an inner fiber core and an outer fiber cladding, the thickness of fiber cladding on the fiber portion which extends through said range of positions being selected to provide significant evanescent wave loss when the cladding is immersed in the liquid;
   a density sensor optical fiber completely immersed in said liquid, said density sensor fiber characterized by an inner fiber core and an outer fiber cladding, the thickness of fiber cladding being selected to provide significant evanescent wave loss when the cladding is immersed in the liquid;
   means for injecting light into said level sensor fiber and for injecting light into said density sensor fiber;
   means for determining a first ratio of input light intensity to the intensity of light which has passed through said level sensor fiber;
   means for determining a second ratio of input light intensity to the intensity of light which has passed through said density sensor fiber; and
   processing means responsive to said first ratio and said second ratio for providing a level signal indicative of the liquid level in said container, said processing means comprising means for compensating the level indicated by the value of said first ratio by the value of said second ratio to compensate said level indication with changes in the density of the liquid.

8. The system of claim 7 wherein said means for determining a first ratio comprises a first photodetector responsive to the intensity of light injected into said level sensor fiber, and a second photodetector responsive to light which has passed through said level detector fiber at least once to provide a second photodetector signal indicative of the intensity of said light which has passed through said level detector fiber at least once.

9. The system of claim 7 wherein said means for determining a second ratio comprises a first photodetector responsive to the intensity of light injected into said density sensor fiber, and a second photodetector responsive to light which has passed through said density sensor fiber at least once to provide a second photodetector signal indicative of the intensity of said light which has passed through said density sensor fiber at least once.

10. The system of claim 7 wherein said light injecting means comprises a semiconductor laser.

11. The system of claim 7 wherein said level sensor optical fiber and said density sensor optical fiber are eccentric core fibers.

12. A method for measuring the level of liquid within a container, comprising a sequence of the following steps:
   disposing a level sensor optical fiber within said container and extending through the range of liquid surface positions to be measured by the system, wherein said fiber is characterized by an inner fiber core and an outer fiber cladding, the thickness of fiber cladding on the fiber portion which extends through said range of positions being selected to provide significant evanescent wave loss when the cladding is immersed in the liquid;
   completely immersing a density sensor optical fiber in said liquid within said container, said density sensor fiber characterized by an inner fiber core and an outer fiber cladding, the thickness of fiber cladding being selected to provide significant evanescent wave loss when the cladding is immersed in the liquid;
   injecting light into said level sensor fiber and into said density sensor fiber;
   determining the loss of light which has passed through said level sensor fiber at least once;
   determining the loss of light which has passed through said density sensor fiber at least once; and
   processing said respective light losses to provide a signal indicative of the liquid level in the container and which is compensated for changes in the density of the liquid level.

13. The method of claim 12 wherein said step of determining the loss of light which has passed through said level sensor fiber comprises the step of determining the ratio of the input light intensity to the intensity of light which has passed through the level sensor fiber at least once.

14. The method of claim 12 wherein said step of determining the loss of light which has passed through said density sensor fiber comprises the step of determining the ratio of the input light intensity to the intensity of light which has passed through the density sensor fiber at least once.

15. A system for measuring characteristics of a parameter of a liquid in a container, comprising:
   a plurality of optical fibers dispersed within said liquid and disposed so that each fiber is fully immersed within said liquid, each said fiber characterized by an inner fiber core and an outer fiber cladding, the cladding thickness appropriate to provide significant evanescent wave loss when the cladding is immersed in the liquid;
   means for injecting light into said plurality of optical fibers;
   means for determining the loss of light traversing each said fiber at least once; and
   processing means responsive to said respective light losses to determine one or more characteristics of said parameter at dispersed locations throughout said liquid.

16. The system of claim 15 wherein said parameter is the liquid density, and said characteristic comprises changes in said density over time.

17. The system of clam 15 wherein said parameter is the liquid temperature, and said characteristic comprises changes in said temperature over time.

18. The system of claim 15 wherein said parameter is the liquid pressure, and said characteristic comprises changes in said pressure over time.

19. The system of claim 15 wherein said plurality of optical fibers are dispersed at different depths within said liquid, wherein said system provides measurements of said characteristics of said parameter at said different depths within said liquid.

20. The system of claim 15 wherein said parameter is the absorption coefficient of light transmitted through said liquid.

* * * * *